US008512753B2

(12) United States Patent
Musa et al.

(10) Patent No.: US 8,512,753 B2
(45) Date of Patent: Aug. 20, 2013

(54) MICRONIZED PARTICLES OF LOW-DOSAGE STRENGTH ACTIVE AGENTS FOR POWDER FORMULATIONS FOR INHALATION

(75) Inventors: Rossella Musa, Parma (IT); Daniela Cocconi, Parma (IT); Silvia Catinella, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 409 days.

(21) Appl. No.: 12/500,204

(22) Filed: Jul. 9, 2009

(65) Prior Publication Data

US 2010/0055192 A1 Mar. 4, 2010

Related U.S. Application Data

(63) Continuation of application No. PCT/IB2007/003892, filed on Dec. 13, 2007.

(30) Foreign Application Priority Data

Jan. 10, 2007 (EP) .................................... 07000425

(51) Int. Cl.
*A61K 9/14* (2006.01)
*A61K 31/135* (2006.01)

(52) U.S. Cl.
USPC .............................. 424/489; 514/649; 424/46

(58) Field of Classification Search
USPC ............................ 424/489, 46; 514/312, 649
See application file for complete search history.

(56) References Cited

U.S. PATENT DOCUMENTS

| | | | | |
|---|---|---|---|---|
| 5,674,860 | A * | 10/1997 | Carling et al. | 514/171 |
| 5,874,063 | A * | 2/1999 | Briggner et al. | 424/45 |
| 6,284,287 | B1 | 9/2001 | Sarlikiotis et al. | |
| 2003/0165436 | A1 | 9/2003 | Staniforth et al. | |
| 2003/0180227 | A1 | 9/2003 | Staniforth et al. | |
| 2005/0175549 | A1 | 8/2005 | Goede et al. | |
| 2007/0202053 | A1* | 8/2007 | Bilzi et al. | 424/46 |

FOREIGN PATENT DOCUMENTS

| | | |
|---|---|---|
| WO | 95/24889 | 9/1995 |
| WO | 01/05429 | 1/2001 |
| WO | 02/00199 | 1/2002 |
| WO | 2005/013963 | 2/2005 |
| WO | WO 2005089717 A1 * | 9/2005 |
| WO | WO 2008084312 A2 * | 7/2008 |

OTHER PUBLICATIONS

Welsh et al., Formoterol vesus short-acting beta agonists s relief medication for adults and children with asthma, Cochrane Database Syst. Rev. Sep. 8, 2010:(9): CD008418 [Downloaded Jun. 11, 2010] [Retrieved from internet <URL: http://www.ncbi.nlm.nih.gov/pubmed/20824877 >], 2 pages.*

International Search Report, WO 2008/084312 A3, PCT/IB2007/003892, (obtained from WIPO website), Sep. 19, 2008, 7 pages.*

(Continued)

*Primary Examiner* — Jason M Sims
*Assistant Examiner* — Miriam A Levin
(74) *Attorney, Agent, or Firm* — Oblon, Spivak, McClelland, Maier & Neustadt, L.L.P.

(57) ABSTRACT

Micronized particles of a low-dosage strength active ingredient, to be used in dry powder formulations for inhalation, with particular properties can easily and homogenously disperse in a dry powder formulation to be administered by means of a dry powder inhaler device.

11 Claims, 6 Drawing Sheets

(56) References Cited

OTHER PUBLICATIONS

International Preliminary Report on Patentability, PCT/IB2007/003892, (obtained from WIPO website), Mar. 23, 2009, 12 pages.*
Written Opinion of the International Searching Authority, PCT/IB2007/003892, (obtained from WIPO website), Date cited is date of ISR: Sep. 19, 2008, 8 pages.*
Wikipedia, Formoterol [Downloaded Jun. 15, 2011] [Retrieved from internet <URL: http://en.wikipedia.org/wiki/Formoterol >], 1 page.*
International Search Report issued Sep. 19, 2008, in PCT/IB07/03892 filed Dec. 13, 2007.
Guchardi et al.,International Journal of Pharmaceutics, vol. 348, pp. 10-17 (2008).
Chew et al., J. Pharm. Pharmaceut. Sci., vol. 5, pp. 162-168 (2002).

* cited by examiner

MICRONIZED PARTICLES OF LOW-DOSAGE STRENGTH ACTIVE AGENTS FOR POWDER FORMULATIONS FOR INHALATION

CROSS REFERENCES TO RELATED APPLICATIONS

This application is a continuation of International Patent Application No. PCT/IB2007/003892, filed on Dec. 13, 2007, and claims priority to European Patent Application No. 07000425.4, filed on Jan. 10, 2007, both of which are incorporated herein by reference in their entireties.

BACKGROUND OF THE INVENTION

1. Field of the Invention

The present invention relates to micronized particles of a low-dosage strength active ingredient for dry powder formulations for inhalation and methods for preparing them. In particular the present invention relates to micronized particles of low-dosage strength active ingredients which can homogeneously and easily disperse in a dry powder formulation to be administered by means of a dry powder inhaler device. The present invention also relates to formulations of such micronized particles in the form of powders for inhalation.

2. Discussion of the Background

The administration of pharmacologically active ingredients by inhalation to the airways is a widely used technique especially for the treatment of reversible airway obstruction, inflammation, and hyperresponsiveness.

This technique is also used for the administration of active agents having systemic action, which are absorbed via the lungs, into the bloodstream. Some of the most widely used systems for the administration of drugs to the airways are the dry powder inhalers (DPIs). Drugs intended for inhalation as dry powders by means of DPIs should be used in the form of particles of few microns (μm) particle size.

Micronized particles generally considered "respirable" are those with a particle size comprised from 0.5 to 10 microns, preferably 0.5 to 5 microns, as they are capable of penetrating into the lower airways, i.e. the bronchiolar and alveolar sites, which are the site of action for the pulmonary drugs and where absorption takes place for the systemic drugs. Larger particles are mostly deposited in the oropharyngeal cavity so they cannot reach said sites, whereas the smaller ones are exhaled.

The desirable particle sizes are generally achieved by grinding or so-called micronization of the active agent.

In the prior art, several documents deal with the physicochemical characteristics of micronized active ingredients for inhalation in particular in terms of particle size (see, US 2004/002510, WO 03/90715, WO 03/24396, WO 02/85326, WO 98/52544, EP 680752, WO 98/17676, and WO 95/01324).

Although micronization of the drug is essential for deposition into the lower respiratory tract during inhalation, it is known that the finer the particles are, the stronger are the cohesion forces that favour the formation of agglomerates.

For this reason, powders for inhalation have been commonly formulated by mixing the micronized drug with a carrier (generally, a physiologically acceptable material, commonly lactose or mannitol, preferably α-lactose monohydrate) consisting of coarser particles to give rise to the so-called "interactive ordered mixtures".

However, the present inventors have verified that agglomerates formation may also occur during the preparation of the "interactive ordered mixtures" i.e. during the blending of the active ingredient fine particles with the coarser excipient particles. The formation of agglomerates among the fine particles of the active ingredient jeopardizes their dispersion onto the surface of the coarse excipient particles and hence it is detrimental to the possibility of achieving a good uniformity of distribution of the active ingredient in the powder mixture and hence a good accuracy of the dose. The formation of agglomerates is particularly critical when a low-dosage strength active ingredient is used, e.g. an active ingredient endowed with particularly high potency which is present in the powder formulation in a very low concentration.

In fact, the lower the active ingredient weight percent concentration based on the total weight of the formulation is, the higher is the detrimental effect of the agglomerates on the uniformity of the active ingredient in the powder blend. The lack of homogeneity of the powder, due to the formation of agglomerates, involves the risk of an over or under dosage. Thus, the agglomeration phenomenon, together with other properties such as high adhesiveness degree, leads to problems in the manufacturing of a powder formulation provided with good dosage reproducibility when administered by DPIs.

WO 2005/089717 discloses avoiding agglomeration by preparing microparticles consisting of a low-dosage strength therapeutically active ingredient and excipient particles with a defined particle size that are obtained by pre-mixing or pre-milling. However the preparation of said microparticles is a time-consuming step. Moreover the present inventors have found that such microparticles can face stability problems after storage of the final formulation.

Thus there remains a need for micronized low-dosage strength active agents to be administered by inhalation with a DPI device which, when formulated as interactive ordered mixtures, can easily and homogeneously disperse in the formulation giving rise to a good uniformity of distribution of the particles and hence an adequate accuracy of the metered dose, together with a good performance in terms of delivered dose and respirable fraction.

SUMMARY OF THE INVENTION

This problem has been solved by tailoring the micronized low-dosage strength active agents to a specific particle size which prevents the agglomeration phenomena.

Accordingly, it is one object of the present invention to provide novel micronized low-dosage strength active ingredients.

It is another object of the present invention to provide novel micronized low-dosage strength active ingredients to be administered by inhalation with a dry powder inhaler (DPI) device.

It is another object of the present invention to provide novel micronized low-dosage strength active ingredients to be administered by inhalation with a dry powder inhaler (DPI) device, which, when formulated as interactive ordered mixture with larger carrier particles, can easily and homogeneously disperse in the formulation giving rise to a good uniformity of distribution of the particles, and hence, an adequate accuracy of the metered dose, together with a good performance in terms of delivered dose and respirable fraction.

It is another object of the present invention to provide novel methods for making such a micronized low-dosage strength active ingredient.

It is another object of the present invention to provided novel DPI which contain such a micronized low-dosage strength active ingredient.

It is another object of the present invention to provide novel methods for treating and/or preventing certain diseases and conditions by administering such a micronized low-dosage strength active ingredient.

These and other objects, which will become apparent during the following detailed description, have been achieved by the inventors' discovery that micronized particles of a low-dosage strength active ingredient wherein: i) no more than 10% of the particles have a volume diameter [d(v,0.1)] lower than 0.8 microns; ii) no more than 50% of particles have a volume diameter [d(v,0.5)] lower than 1.7 microns; and iii) at least 90% of the particles have a volume diameter lower than 10 microns exhibit excellent properties.

The invention also provides a method for preparing the micronized particles of the invention.

In an another aspect, the present invention provides dry powder formulations to be administered using a dry powder inhaler device which contains the micronized particles of the present invention and particles of a physiologically acceptable excipient having a mass median diameter (MMD) higher than 90 micron.

In a further aspect, the present invention provides powder formulations to be administered using a dry powder inhaler device which contains micronized particles of an active ingredient having a nominal dose delivered after each actuation of the inhaler equal or lower than 4 µg and particles of a physiologically acceptable excipient having a mass median diameter (MMD) higher than 90 micron wherein agglomerates of micronized particles of said active ingredient are absent as determined by Near Infrared Spectrophotometer provided with a microscope.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1A:
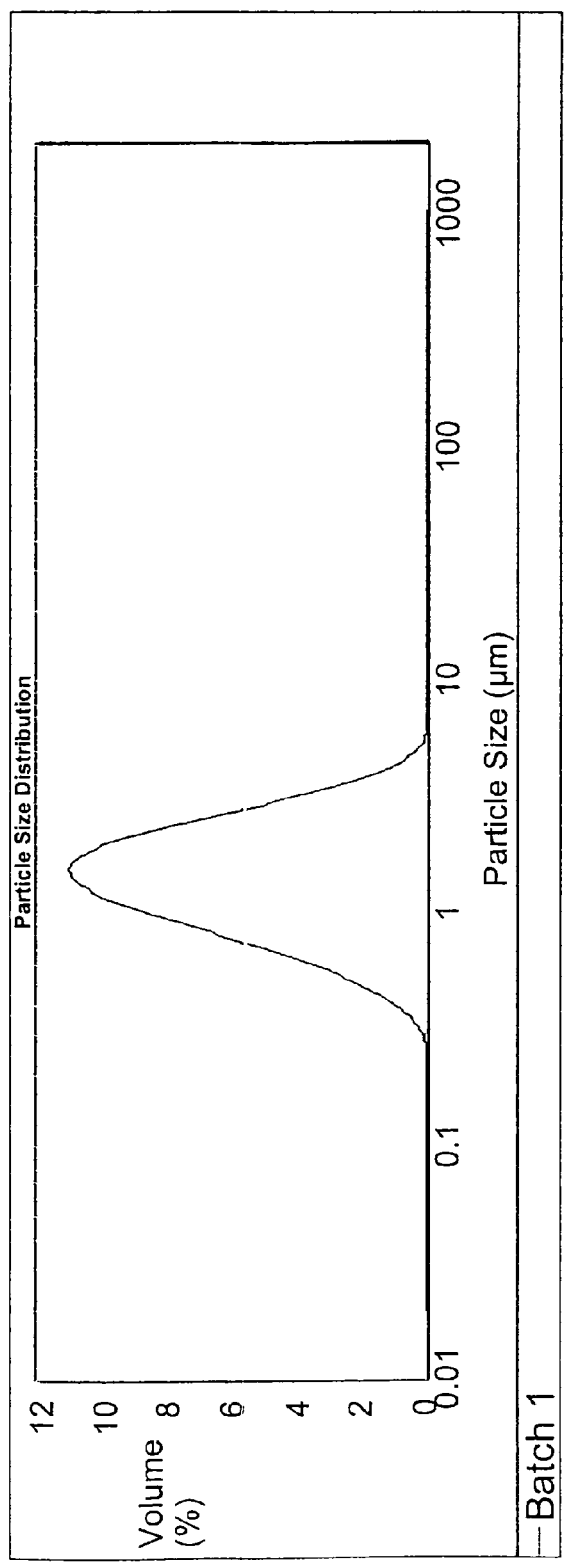
FIG. 1 shows the particle size distribution of six different batches of micronised carmoterol hydrochloride (1, 2, 3, 4, 5, and 6).

In the contest of the present invention, the terms "active ingredient", "active agent" and "active substance" are used as synonyms.

As used herein, the term "low-dosage strength active ingredient" means an active ingredient to be delivered using a dry powder inhaler (DPI) device whose nominal dose delivered after each actuation of the inhaler is equal to or lower than 20 µg, advantageously equal to or lower than 12 µg, preferably equal to or lower than 6 µg, more preferably equal to or lower than 4 µg, even more preferably lower than 2 µg.

In the context of the present application, the particle size is quantified by measuring a characteristic equivalent sphere diameter, known as volume diameter by laser diffraction. The volume diameter (VD) is related to the mass diameter (MD) by the density of the particles (assuming a size independent density for the particles). Particle size distribution is described by: i) the volume median diameter (VMD) or the mass median diameter (MMD) which corresponds to the diameter of 50 percent by weight or volume respectively, of the particles, and ii) the VD (MD) in microns of 10% and 90% of the particles.

Upon aerosolization, the particle size is expressed as mass aerodynamic diameter (MAD) and the particle size distribution as mass median aerodynamic diameter (MMAD). The MAD indicates the capability of the particles of being transported suspended in an air stream. The MMAD corresponds to the mass aerodynamic diameter of 50 percent by weight of the particles.

The micronized particles of the invention will comprise at least one low dosage strength active substance that can be delivered to the lungs in form of a powder for inhalation. The active substance may act either locally, at the pulmonary level, or, after passage in the bloodstream, at the systemic level. The active agents advantageously consist essentially of one or more therapeutically active agents. Suitable therapeutically active ingredients include those which are usually administered orally by inhalation for the treatment of diseases such as respiratory diseases. Examples of high potent active substance in the respiratory field are the long-acting $\beta_2$-agonists such as formoterol, salmeterol, indacaterol, arformoterol, and 8-hydroxyhydroxy-5-[(1R)-1-hydroxy-2-[[(1R)-2-(4-methoxyphenyl)-1-methylethyl]amino]ethyl-2(1H)-quinolinone, also reported in the following with the international non-proprietary name carmoterol.

References herein to any active agent are to be understood to include any physiologically acceptable derivative.

In the case of the $\beta_2$-agonists, physiologically acceptable derivatives include salts, solvates, and solvates of salts.

In a particular embodiment, the low dosage strength active substance is carmoterol which is preferably used in the form of a hydrochloride salt.

In another particular embodiment, the low dosage strength active substance is a physiologically acceptable salt formoterol. The salts of formoterol also include the relevant enantiomeric salts of (R,R)-formoterol, (S,S)-formoterol, (R,S)-formoterol, (S,R)-formoterol, and the mixtures thereof, while the racemic mixture of (R,R)-formoterol, and (S,S)-formoterol is of particular importance. Said racemic mixture of formoterol is preferably used in the form of a fumarate salt, more preferably in the form of the dihydrate fumarate.

Otherwise, the active ingredient may be selected from low-dosage strength active ingredients for systemic use, for example peptides or a polypeptides such as cyclosporin, insulin, human growth hormone, calcitonin, and erythropoietin, or decoy or antisense oligonucleotides.

Advantageously the particle size of the active ingredient is determined by measuring the characteristic equivalent sphere diameter, known as volume diameter, by laser diffraction as described above, preferably using a Malvern or an equivalent apparatus.

Advantageously no more than 10% of the particles of the micronized active ingredient have a volume diameter [d(v, 0.1)] lower than 0.8 microns, preferably lower than 0.9 microns, more preferably lower than 1 micron. Advantageously no more than 50% of particles have a volume diameter [d(v,0.5)] lower than 1.7 microns, preferably lower than 1.9 microns, more preferably lower than 2 microns.

Advantageously at least 90% of the particles have a volume diameter lower than 10 microns, preferably lower than 8 microns, more preferably lower than 6 microns, even more preferably lower than 5.5 microns.

In another embodiment, at least 90% of the particles have a volume diameter lower than 4.5 microns.

In one embodiment of the invention, the micronized low-dosage strength active ingredient has no more than 5% of particles with a volume diameter [d(v,0.05)] lower than 0.65 microns, preferably lower than 0.7 microns.

Advantageously, the particles have a particle size spread, defined as [d(v,0.9)−d(v,0.5)]/d(v,0.5) is higher than 1.4 and lower than 2, preferably higher than 1.5 and lower than 1.8.

The micronized particles of the low-dosage strength active ingredient of the invention show little or no tendency to aggregation.

It has indeed been found that a particle size fulfilling the aforementioned requirements is optimal for avoiding the formation of stable agglomerates when the particles of a micronized low-dosage strength active ingredient are mixed with the coarse carrier particles to form interactive ordered mixtures.

In particular, when the particles have d(v, 0.1) and d(v, 0.5) moving towards finer size, i.e. less than 0.8 micron and less than 1.7 micron, respectively, they give rise to stable agglomerates which cannot be dispersed even after a long time of mixing (more than 10 hours). This is detrimental to the uniformity of distribution of the active ingredient in the final formulation.

The agglomerates of the active ingredient in the formulations can be detected by a Near Infrared Spectrophotometer provided with a microscope.

Once formulated as interactive ordered mixtures, the micronized low-dosage strength active agent of the invention gives rise, upon aerosolization, to particles having a MMAD equal or higher than 1.7 microns, preferably higher than 1.9 microns, more preferably higher than 2 microns.

The micronized low-dosage strength active ingredients of the present invention may be completely amorphous or crystalline. Preferably, it is crystalline or substantially crystalline, e.g. with an amorphous content lower than 5% w/w, preferably lower than 3% w/w was determined by isothermal gas perfusion calorimetry.

Also characteristic of the micronized low-dosage strength active ingredients of the present invention is the specific surface area which in turn depends on the physico-chemical characteristics of the active ingredient, its density and its particle size distribution.

In the case of crystalline carmoterol hydrochloride, the specific surface area is advantageously comprised between 8 and 12 $m^2/g$, preferably between 8.5 and 10.5 $m^2/g$, more preferably between 9.5 and 10 $m^2/g$, while in the case of formoterol fumarate dehydrate it is advantageously comprised between 5 and 7.5 $m^2/g$, preferably between 5.2 and 6.5 $m^2/g$, more preferably between 5.5 and 5.8 $m^2/g$.

The Specific Surface Area may be determined by Brunauer-Emmett-Teller (BET) nitrogen adsorption method according to a procedure well known to the person skilled in the art.

The micronized low-dosage strength active ingredient of the invention is preferably used in a substantially pure form, e.g., higher than 95% w/w, more preferably higher than 98% w/w, even more preferably higher than 99% w/w, and it preferably contains low levels of residual solvents, for example less than 1% w/w, preferably less than 0.5% w/w.

The micronized low-dosage strength active ingredients of the invention may be prepared by grinding in a suitable mill or by other techniques such as spray-drying or techniques based on the use of gases compressed and/or in supercritical conditions.

Preferably they are prepared by grinding using a conventional fluid energy mill such as the jet mill apparatus. Depending on the type of the apparatus and size of the batch, the person skilled in the art shall suitably adjust the milling parameters such as the operating pressure and the feeding rate to achieve the desired particle size.

Advantageously the operating pressure is less than 10 bar, preferably comprised between 7 and 9 bar. Preferably, the micronization is carried out with the exclusion of moisture, more preferably using an inert gas such as nitrogen.

In another aspect, the present invention provides powder formulations for inhalation in the form of interactive ordered mixtures characterized in that they contain micronized particles of a low-dosage strength active agent according to the present invention.

Advantageously, a powder formulation for inhalation may comprise micronized particles of a low-dosage strength active agent according to the present invention and coarse particles of a physiologically acceptable excipient, e.g. particles having a MMD higher than 90 microns and preferably a MD comprised between 50 microns and 500 microns, more preferably between 150 and 400 microns, even more preferably between 210 and 355 microns.

The coarse excipient particles preferably have a relatively highly fissured surface, that is, on which there are clefts and valleys and other recessed regions, referred to herein collectively as fissures.

The "relatively highly fissured" surface of the coarse excipient particles may be defined in terms of fissure index or rugosity coefficients as disclosed in WO 01/78695 and WO 01/78693 and they can be characterized according to the description therein reported.

Preferably, the powder formulation may further comprises a fraction of microparticles having a MMD lower than 35 microns composed of particles of a physiologically acceptable excipient and an additive material selected from the class of the anti-adherents such as the aminoacids leucine and isoleucine or of the lubricants such as magnesium stearate; sodium stearyl fumarate, stearyl alcohol, stearic acid, and sucrose monopalmitate.

More preferably, the powder formulation comprises a fraction of microparticles having a MMD lower than 15 microns, preferably lower than 10 microns, composed of particles of a physiologically acceptable excipient and particles of magnesium stearate according to the teaching of EP 1274406.

Magnesium stearate is added to the formulation with the aim of improving the respirable fraction of the active substance.

The physiologically acceptable excipient may be constituted of any amorphous or crystalline physiologically acceptable inert material of animal or vegetal source or combination thereof. Preferred materials are crystalline sugars and for example monosaccharides such as glucose or arabinose, or disaccharides such as maltose, saccharose, dextrose, or lactose. Polyalcohols such as mannitol, sorbitol, maltitol, lactitol may also be used. the most preferred material is α-lactose monohydrate.

Examples of commercially available lactose are Capsulac® and Pharmatose®. An example of commercially available mannitol is Pearlitol®.

In a preferred embodiment, the fraction of microparticles is composed of 98% by weight of α-lactose monohydrate and 2% by weight of magnesium stearate and the ratio between the fraction of microparticles and the fraction of coarse particles made of α-lactose monohydrate particles is 10:90% by weight, respectively.

The amount of magnesium stearate in the final formulation is advantageously comprised between 0.02% and 1.0% by weight, preferably between 0.05 and 0.5% by weight, more preferably between 0.1 and 0.4% by weight, based on the total weight of the formulation.

If desired, the powder formulation for inhalation may comprise an additional active ingredient in form of micronized particles selected from the group of corticosteroids such as budesonide and its epimers, beclometasone dipropionate, triamcinolone acetonide, fluticasone propionate, flunisolide, mometasone furoate, rofleponide and ciclesonide; the group of anticholinergic/or M3-receptor antagonistantimuscarinic agents such as ipratropium bromide, oxytropium bromide, tiotropium bromide, glycopyrrolate bromide and its enantiomers; the group of phosphodiesterase-4 (PDE-4) inhibitors such as cilomilast and roflumilast, and their combinations, provided that they are compatible with one another under conditions of storage and use.

Advantageously, at least 90% of the particles of the additional active ingredient have a particle size less than 10 microns, preferably less than 6 microns. More preferably, the additional active ingredient has the same particle size distribution of the low-dosage strength active ingredient of the invention.

In a particular embodiment of the invention, a combination of carmoterol with budesonide is preferably used.

The powder formulations for inhalation containing a micronized low-dosage strength active ingredient according to the invention are characterized by a high degree of homogeneity. After the mixing, the content uniformity of the active ingredient, expressed as relative standard deviation (RSD), is less than 5%, preferably equal/less than 2.5%, more preferably equal or less than 1.5%.

Said powder formulations may be utilized with any type of DPIs known in the art. DPIs can be divided into two basic types: i) single dose inhalers, for the administration of pre-subdivided single doses of the active compound; ii) multidose dry powder inhalers (MDPIs), either with pre-subdivided single doses or pre-loaded with quantities of active ingredient sufficient for multiple doses. On the basis of the required inspiratory flow rates (l/min) which in turn are strictly depending on their design and mechanical features, DPIs are divided in: i) low-resistance devices (>90 l/min); ii) medium-resistance devices (about 60 l/min); iii) high-resistance devices (about 30 l/min). The powder formulation of the invention is preferably administered with a medium- or a high-resistance multidose device.

Other features of the invention will become apparent in the course of the following descriptions of exemplary embodiments which are given for illustration of the invention and are not intended to be limiting thereof.

EXAMPLES

Example 1

Preparation of Different Batches of Micronized Particles of Carmoterol Hydrochloride as Active Ingredient by Grinding Different batches of carmoterol hydrochloride were milled in a jet mill apparatus at different operating conditions in order to obtain different particle size distribution. The micronized batches were characterised in terms of particle size distribution and Specific Surface Area.

The particle size was determined by laser diffraction using a Malvern apparatus. The parameters taken into consideration were the VD in microns of 5%, 10%, 50%, and 90% of the particles expressed as d(v,0.05), d(v,0.1), d(v, 0.5), and d(v, 0.9), respectively, which correspond to the mass diameter assuming a size independent density for the particles. The Specific Surface Area (SSA) was determined by BET nitrogen adsorption using a Coulter SA3100 apparatus as a mean of three determinations. The relevant data are reported in Table 1.

Figure 1B:
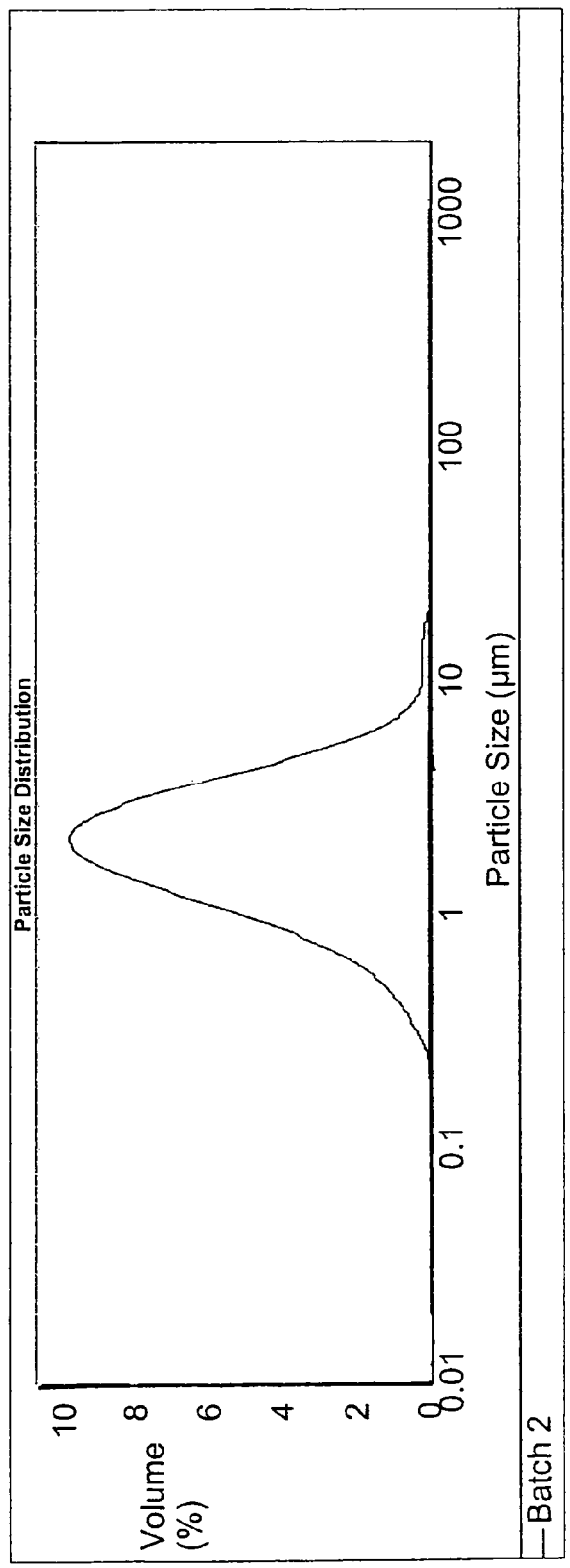
Figure 1C:
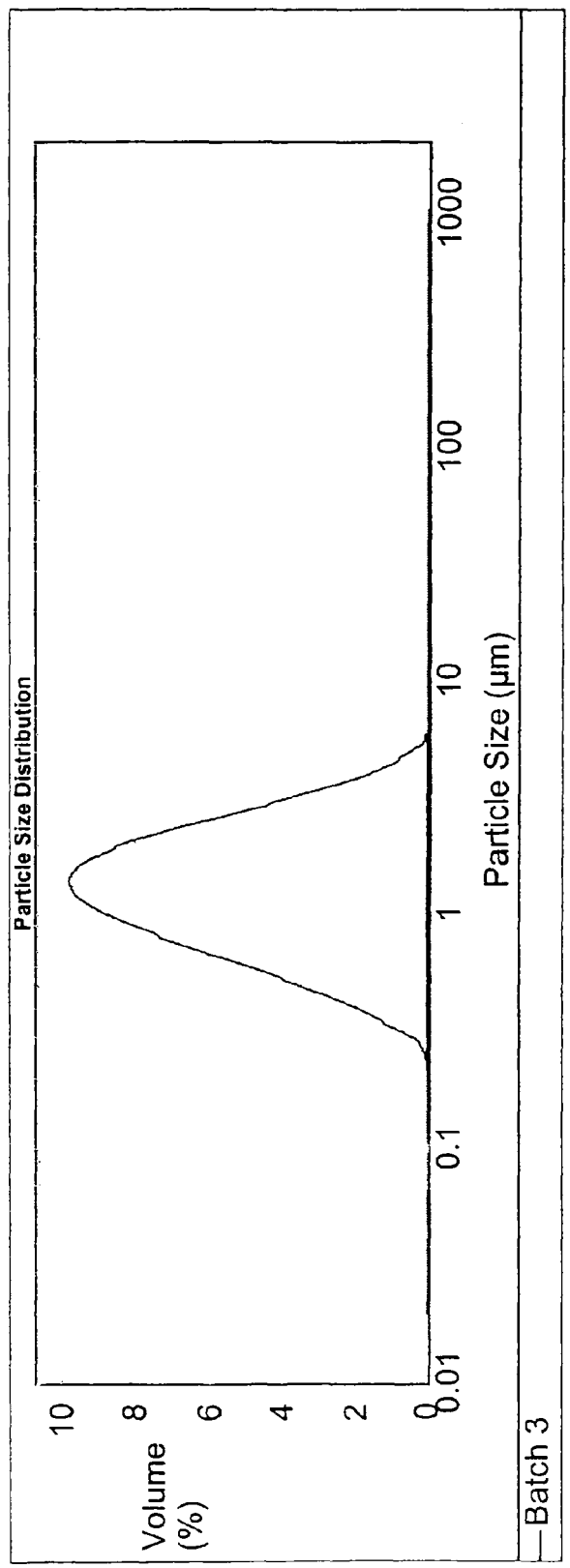
Figure 1D:
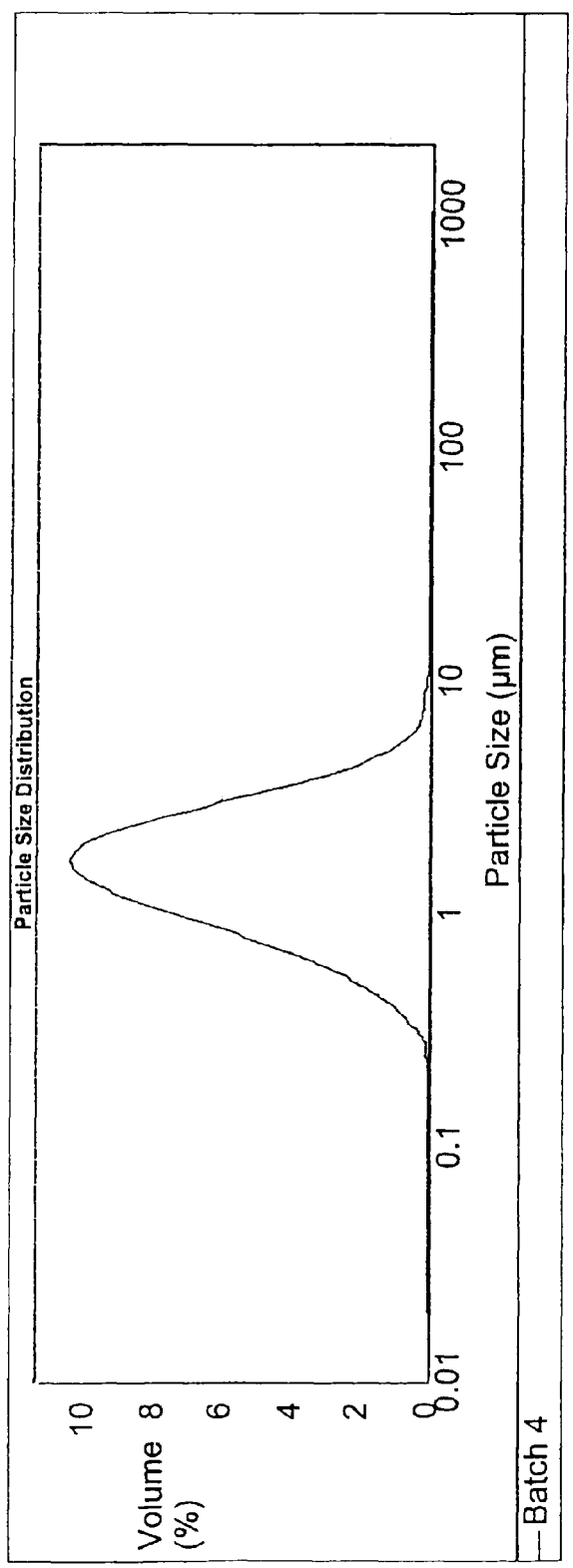
Figure 1E:
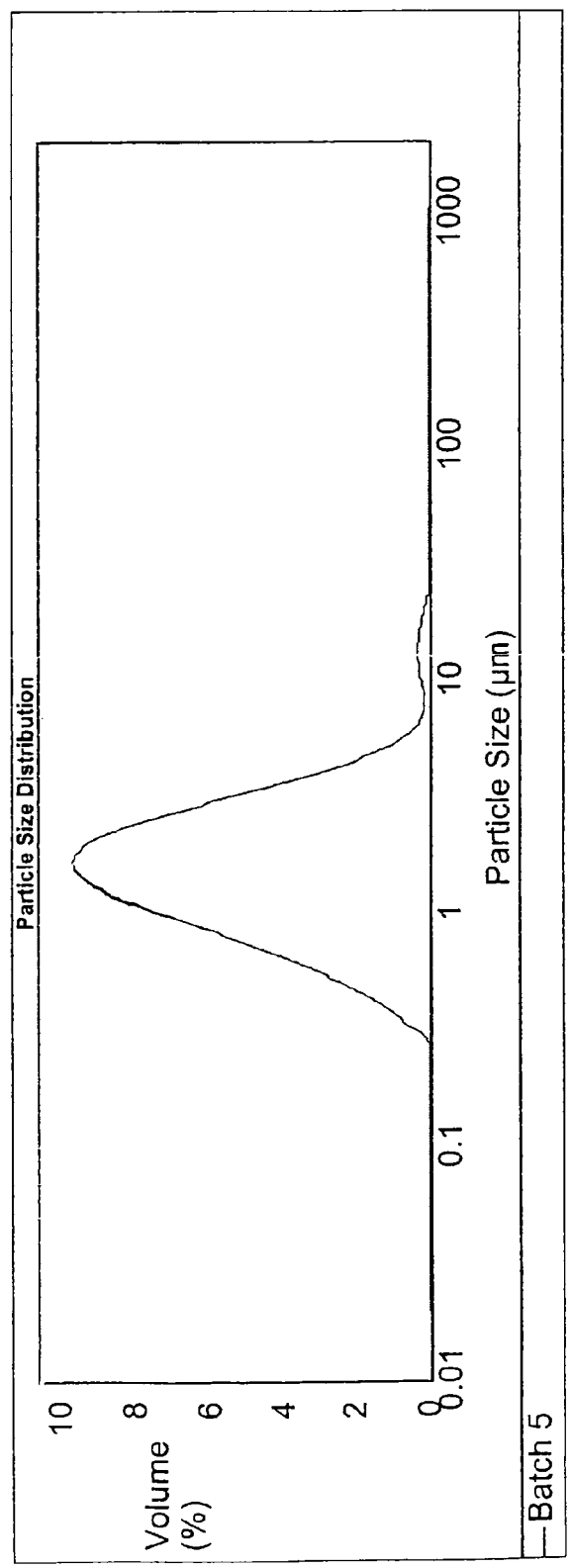
Figure 1F:
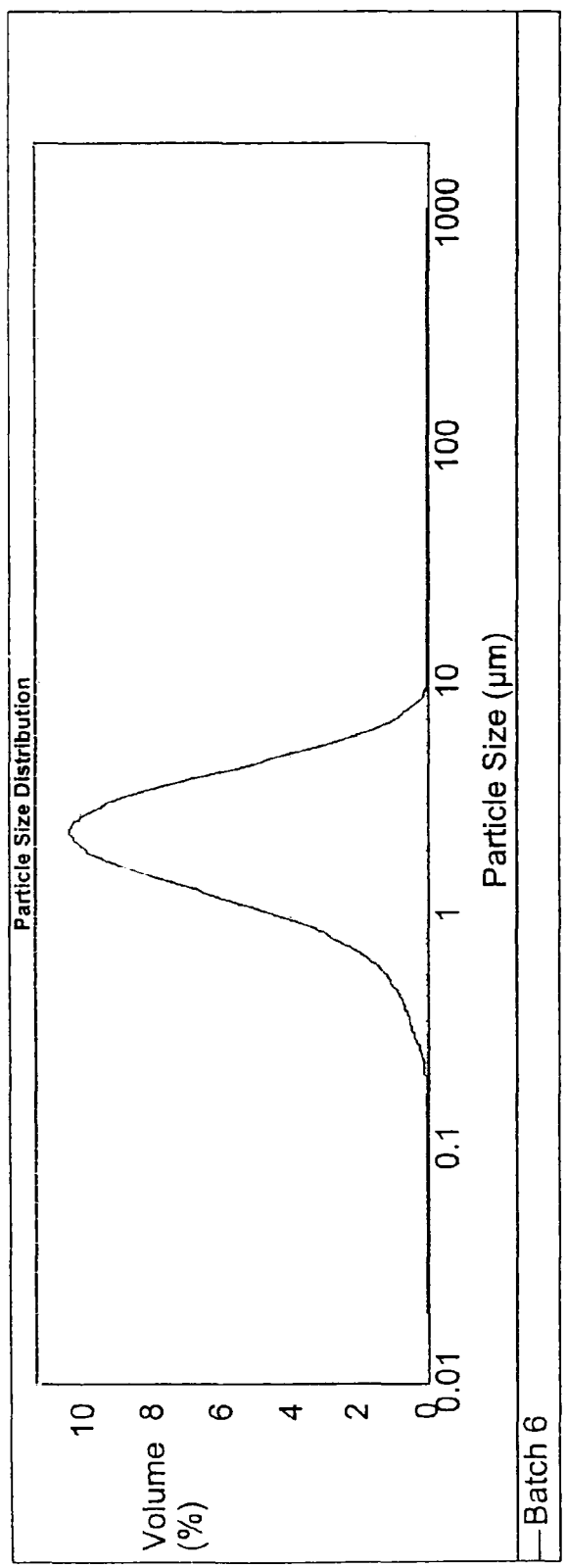

The particle size distribution of the six different batches of micronized carmoterol hydrochloride is reported in FIG. 1. On the X- and Y-axis, the diameter of the particles expressed in microns and the percent of the particles on the total volume of the particles are reported, respectively.

TABLE 1

Particle size distribution and Specific Surface Area (SSA) of the different batches of micronized carmoterol hydrochloride.

| Particle size (μm) | Batch 1 | Batch 2 | Batch 3 | Batch 4 | Batch 5 | Batch 6 |
|---|---|---|---|---|---|---|
| d (v, 0.05) | 0.70 | 0.67 | 0.58 | 0.55 | 0.48 | 0.59 |
| d (v, 0.1) | 0.94 | 0.85 | 0.59 | 0.68 | 0.70 | 0.73 |
| d (v, 0.5) | 2.16 | 2.03 | 1.32 | 1.58 | 1.45 | 1.61 |
| d (v, 0.9) | 4.34 | 4.31 | 2.75 | 3.40 | 2.75 | 3.25 |
| SSA ($m^2/g$) | 9.70 | 9.68 | 18.11 | 10.74 | 11.91 | 11.80 |

As can be appreciated from Table 1, different particle size distributions of the micronized batches and different Specific Surface Area values were obtained, by varying the operating pressure.

The various batches were then added to a carrier made of coarser particles. The agglomerates in the formulations were detected by a Near Infrared Spectrophotometer provided with a microscope and thy turned out to be constituted of particles of the active ingredient.

Batches 1 and 2, which have no more than 10% of the particles with a mass diameter lower than 0.8 microns and no more than 50% of particles with a mass diameter lower than 2 microns, uniformly dispersed into the carrier and after a suitable time of mixing no agglomerates were observed. In the formulations prepared starting from batches 3, 4, and 5, constituted of particles having more than 10% of the particles with a mass diameter lower than 0.8 microns and more than 50% of the particles with a mass diameter lower than 1.7 microns, agglomerates where still present after longer period, i.e. ten hours of mixing.

It follows that micronized particles of an active ingredient having the d(v, 0.1) and d(v, 0.5) of the particles moved towards finer size, i.e. less than 0.8 microns and less than 1.7 microns, respectively, give rise to stable agglomerates which cannot be dispersed even after long time of mixing (more than 10 hours). This is detrimental to the uniformity of distribution of the active ingredient in the final formulation.

Example 2

Preparation of Different Batches of Micronized Particles of Formoterol Fumarate Dihydrate as Active Ingredient by Grinding Different batches of formoterol fumarate dihydrate were milled in a jet mill apparatus at different operating conditions in order to obtain different particle size distribution. The micronized batches were characterised in terms of particle size distribution and Specific Surface Area as reported in Example 1. The relevant data are reported in Table 2.

TABLE 2

Particle size distribution and Specific Surface Area (SSA) of the different batches of micronized of formoterol fumarate dehydrate.

| Particle size (μm) | Batch 1 | Batch 2 | Batch 3 | Batch 4 | Batch 5 |
|---|---|---|---|---|---|
| d (v, 0.1) | 1.41 | 1.68 | 1.66 | 0.61 | 0.60 |
| d (v, 0.5) | 2.58 | 2.93 | 2.90 | 2.09 | 2.27 |
| d (v, 0.9) | 4.60 | 5.08 | 5.02 | 5.28 | 5.14 |
| SSA (m$^2$/g) | 5.73 | 5.82 | 5.54 | — | 7.90 |

As can be appreciated from Table 2, different particle size distributions of the micronized batches and different Specific Surface Area values were obtained, varying the operating pressure.

The various batches were then added to a carrier made of coarser particles. Batches 1, 2, and 3, which have no more than 10% of the particles with a mass diameter lower than 1.4 microns, uniformly dispersed into the carrier and after a suitable time of mixing no agglomerates were observed. In the formulations prepared starting from batches 4 and 5, constituted of particles having more than 10% of the particles with a mass diameter lower than 0.7 microns, agglomerates where still present after longer period, i.e. ten hours of mixing.

Example 3

"Interactive Ordered Mixture" Formulation Containing Micronised Carmoterol Hydrochloride Batch 2, a Fraction of Microparticles, and a Fraction of Coarse Particles a) Preparation of the Fraction of Microparticles.

α-lactose monohydrate SpheroLac® 100 with a starting mass diameter of 50 to 400 microns (MMD of about 170 microns) and magnesium stearate with a starting mass diameter of 3 to 35 microns (MMD of about 10 microns) in the ratio 98:2 percent by weight were co-milled in a jet mill apparatus.

b) Addition of the Fraction of Microparticles to the Fraction of Coarse Particles.

89.5 percent by weight of α-lactose monohydrate Capsu-Lac® (212-355 microns) was placed in a 240 ml stainless steel container, then 10 percent by weight of the fraction of microparticles was added. The blend was mixed in a Turbula mixer for 2 hours at 42 r.p.m. to obtain the carrier.

c) Addition of the Micronized Active Ingredient

Micronized carmoterol hydrochloride batch 1 of Example 1 was added to the carrier in a suitable amount in order to obtain a ratio of 1 μg of active ingredient to 10 mg of final formulation and mixed in a Turbula mixer for one hours at 32 r.p.m.

Example 4

Characterisation of the Formulation of Example 3

The formulation of Example 3 was characterised in terms of the uniformity of distribution of the active ingredient and aerosol performances after loading it in a multidose dry powder inhaler. The uniformity of distribution of the active ingredient was evaluated by withdrawing 10 samples, each equivalent to about from one to three doses, from different parts of the blend and evaluated.

The evaluation of the aerosol performance was carried out using a Multi Stage Liquid Impinger (MSLI) apparatus (Apparatus C) according to the conditions reported in the Eur Ph 4$^{th}$ Ed 2004, par 2.9.18, pages 213-219. After aerosolization of 10 doses, the MSLI apparatus was disassembled and the amounts of drug deposited in the stages were recovered by washing with a solvent mixture and then quantified by High-Performance Liquid Chromatography (HPLC). The following parameters, were calculated: i) the delivered dose, which is the amount of drug delivered from the device recovered in the impactor; ii) the fine particle dose (FPD), which is the amount of delivered dose recovered below 5 micron; iii) the fine particle fraction (FPF), which is the percentage of the fine particle dose relative to the delivered dose reaching the stage 2 of TSI; and iv) the MMAD. The results are reported in Table 3.

TABLE 3

Uniformity of distribution of the active ingredient and aerosol performances.

| | |
|---|---|
| Uniformity of distribution of the active ingredient (%, RSD) | 97.2 (1.1) |
| Delivered dose (μg) | 0.9 |
| FPD (μg) | 0.5 |
| FPF (%) | 56.0 |
| MMAD (μm) | 2.0 |

The formulation prepared using the micronized active ingredient of the invention shows an excellent uniformity of distribution of the active ingredient as demonstrated by the low RSD. The aerosol performances of the formulation are very good with more than 50% of FPF.

Example 5

An analogous formulation to that of Example 3 was prepared but micronized formoterol fumarate dihydrate batch 1 of Table 1 instead of carmoterol hydrochloride was used as active ingredient. Said active ingredient was added to the carrier in a suitable amount in order to obtain a ratio of 6 μg of active ingredient to 10 mg of final formulation. Said formulation as well shows an excellent uniformity of distribution of the active ingredient (RSD lower than 1.5%) and the aerosol performances are very good with more than 50% of FPF.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. Micronized crystalline particles consisting of formoterol fumarate dehydrate, wherein:
   (i) no more than 10% of said particles have a volume diameter [d(v,0.1)] lower than 0.8 micron;
   (ii) no more than 50% of said particles have a volume diameter [d(v,0.5)] lower than 1.7 micron;
   (iii) at least 90% of said particles have a volume diameter [d(v,0.9)] lower than 10 micron,
   (iv) a ratio [d(v,0.9)−d(v,0.5)]/d(v,0.5) is 1.4 to 2.0 micron; and
   said particles have a specific surface area of 5.2 to 6.5 m$^2$/g.

2. Micronized particles according to claim 1, wherein no more than 10% of said particles have a volume diameter lower than 1.0 micron.

3. Micronized particles according to claim 1, wherein no more than 50% of particles have a volume diameter lower than 2.0 micron and higher than 3.0 micron.

4. A powder formulation, comprising micronized particles according to claim 1, and particles of a physiologically acceptable excipient having a mass median diameter, MMD, higher than 90 microns.

5. A powder according to claim 4, which is contained in a multidose dry powder inhaler.

6. A powder according to claim 4, further comprising a fraction of microparticles having a MMD lower than 15 microns and comprising consisting of a mixture of particles of a physiologically acceptable excipient and magnesium stearate.

7. A powder according to claim 6, wherein said physiologically acceptable excipient is:

(a) one or more sugars selected from the group consisting of glucose, arabinose, maltose, saccharose, dextrose, and lactose; or (b) one or more polyalcohols selected from the group consisting of mannitol, maltitol, lactitol, and sorbitol.

8. A powder according to claim 7, wherein said physiologically acceptable excipient is alpha-lactose monohydrate.

9. A powder according to claim 4, further comprising another drug selected from the group consisting of a corticosteroid, an anticholinergic/antimuscarinic agent, a phosphodiesterase-4 (PDE-4) inhibitor, and a combination thereof.

10. A powder according to claim 9, wherein said corticosteroid is selected from the group consisting of budesonide, an epimer of budesonide, beclometasone dipropionate, mometasone furoate, flunisolide, ciclesonide, rofleponide, fluticasone propionate, and triamcinolone acetonide.

11. A powder according to claim 9, wherein said anticholinergic/antimuscarinic agent is selected from the group consisting of ipratropium bromide, oxytropium bromide, tiotropium bromide, glycopyrrolate bromide, and an enantiomer of glycopyrrolate bromide.

* * * * *